:::

United States Patent [19]

Obara et al.

[11] Patent Number: 5,928,876
[45] Date of Patent: *Jul. 27, 1999

[54] PEPTIDE AND COLLAGEN CONTRACTION INHIBITOR

[75] Inventors: Masanobu Obara, Hiroshima; Masaaki Ono, Ibaraki; Katsutoshi Yoshizato, Hiroshima, all of Japan

[73] Assignee: Japan Science and Technology Corporation, Saitama, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/727,311

[22] Filed: Oct. 8, 1996

[51] Int. Cl.⁶ .................................................. G01N 33/53
[52] U.S. Cl. ................ 435/7.1; 514/14; 514/17; 530/327; 530/329
[58] Field of Search ..................... 530/300, 329, 530/327; 514/14, 17; 435/7.1

[56] References Cited

FOREIGN PATENT DOCUMENTS

WO90/13306  11/1990  WIPO .............................. A61K 37/02

*Primary Examiner*—Christina Y. Chan
*Assistant Examiner*—Patrick J. Nolan
*Attorney, Agent, or Firm*—Wenderoth, Lind & Ponack, L.L.P.

[57] ABSTRACT

This invention provides a collagen contraction inhibitor, which contains a peptide comprising at least the amino acid sequence of Sequence ID No. 1, its pharmacologically acceptable derivatives, its pharmacologically acceptable salts or a mixture thereof. This peptide specifically inhibits the binding between collagen and fibronectin by the antagonistic action, providing superb effect in the treatment of cheloid and vulnera.

6 Claims, 1 Drawing Sheet

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

```
Gly Arg Glu Ser Lys Pro
 1               5
```

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Gly Arg Glu Ser Lys Pro Leu Thr Ala Gln Gln Thr Thr Lys
 1               5                  10
```

(2) INFORMATION FOR SEQ ID NO:3:

(i) SEQUENCE CHARACTERISTICS:
        (A) LENGTH: 269 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:3:

```
Ser Asp Thr Val Pro Ser Pro Arg Asp Leu Gln Phe Val Glu Val
 1               5                  10                  15

Thr Asp Val Lys Val Thr Ile Met Trp Thr Pro Pro Glu Ser Ala
                20                  25                  30

Val Thr Gly Tyr Arg Val Asp Val Ile Pro Val Asn Leu Pro Gly
                35                  40                  45

Glu His Gly Gln Arg Leu Pro Ile Ser Arg Asn Thr Phe Ala Glu
                50                  55                  60

Val Thr Gly Leu Ser Pro Gly Val Thr Tyr Tyr Phe Lys Val Phe
                65                  70                  75

Ala Val Ser His Gly Arg Glu Ser Lys Pro Leu Thr Ala Gln Gln
                80                  85                  90

Thr Thr Lys Leu Asp Ala Pro Thr Asn Leu Gln Phe Val Asn Glu
                95                  100                 105

Thr Asp Ser Thr Val Leu Val Arg Trp Thr Pro Pro Arg Ala Gln
                110                 115                 120

Ile Thr Gly Tyr Arg Leu Thr Val Gly Leu Thr Arg Arg Gly Gln
                125                 130                 135

Pro Arg Gln Tyr Asn Val Gly Pro Ser Val Ser Lys Tyr Pro Leu
                140                 145                 150
```

```
Arg Asn Leu Gln Pro Ala Ser Glu Tyr Thr Val Ser Leu Val Ile
            155                 160                 165

Lys Gly Asn Gln Glu Ser Pro Lys Ala Thr Gly Val Phe Thr Thr
            170                 175                 180

Leu Gln Pro Gly Ser Ser Ile Pro Pro Tyr Asn Thr Glu Val Thr
            185                 190                 195

Glu Thr Thr Ile Val Ile Thr Trp Thr Pro Ala Pro Arg Ile Gly
            200                 205                 210

Phe Lys Leu Gly Val Arg Pro Ser Gln Gly Gly Glu Ala Pro Arg
            215                 220                 225

Glu Val Thr Ser Asp Ser Gly Ser Ile Val Val Ser Gly Leu Thr
            230                 235                 240

Pro Gly Val Glu Tyr Val Tyr Thr Ile Gln Val Leu Arg Asp Gly
            245                 250                 255

Gln Glu Arg Asp Ala Pro Ile Val Asn Lys Val Val Thr Pro
            260                 265
```

PEPTIDE AND COLLAGEN CONTRACTION INHIBITOR

FIELD OF THE INVENTION

The present invention relates to a peptide and a collagen contraction inhibitor. It relates more particularly to a novel peptide which functions to specifically inhibit the bindings of collagen fiber with fibronectin which are the substances called extracellular matrix necessary to the binding and supporting of living cells, and to a collagen contraction inhibitor which contains the peptide as its effective constituent and is highly effective in the treatment of keloid scars and wounds.

DESCRIPTION OF PRIOR ART

In animals, cells and extracellular matrix are responsible for maintaining a shape inherent to their respective species, and a variety of proteins and fibrous substances are known as extracellular matrix substances, with collagen being the major protein of the animal connective tissue cells (e.g., skin, blood vessel, sinew, bone and teeth). The collagen serves as a support substance for cells and hence play an important role in the formation and construction of these tissues. By virtue of this ability to support cells, collagen has traditionally been utilized as substrate for cell culture, and recently they are drawing attention as medical materials, such as artificial skin, antemorrhagic, artificial vessel, adherence prevention film, or contact lense for extended use.

It is expected, on the other hand, that if the function of collagen molecule, especially the pattern of combination between cells and collagen are elucidated, then it will provide extremely significant information in the understanding of molecular mechanisms for the formation of organs and tissues in the process of generation of living organisms. On the medical side, they are expected to provide a new clue to the elucidation of development mechanisms of cheloid and vulnera which are considered ascribable to abnormal combination between cells and collagen or to the excessive contraction of collagen fiber.

In this connection, the present inventors prepared a monoclonal antibody (A3A5) which specifically inhibits the combination between collagen and fibroblast, and have found out that the epitope of this antibody exists in the cellular fibronectin, and that the collagen gel contractive system, responsible for the three dimensional formation of cells, is due to the interactions among collagens, fibronectin and fibroblast (Experimental Cell Research, 193, 167–174, 1991).

As has been described above, the studies heretofore conducted by the present inventors have revealed that the collagen, one of the extracellular matrix proteins which plays an important role in the formation and maintenance of living organisms, recognizes the fibronectin produced from cells, and that the specific combination of the two results in the maintenance of the three dimensional structure of cells.

These findings also suggest the possibilities of artificial control over the interaction between collagens and fibronectin as well as the possibilities of novel methods for treatment of keloid scars and wounds.

SUMMARY OF THE INVENTION

An object of the present invention is, therefore, to provide a novel peptide which is in substantially the same domain as that of fibronectin to which collagen recognize, and which antagonisticly inhibits the binding between the collagens and the fibronectin. Another object of the present invention is to provide a collagen contraction inhibitor which contains the peptide as its effective constituent.

The present invention provides a peptide, which comprises at least the amino acid sequence of Sequence ID No. 1.

The present invention also provides a collagen contraction inhibitor, which contains a peptide comprising at least the amino acid sequence of Sequence ID No. 1, its pharmacologically acceptable derivatives, its pharmacologically acceptable salts, or a mixture thereof.

The advantage of the peptide of the present invention is to accelerate the elucidation of the molecular mechanisms for the interactions between cells and extracellular matrix molecules. The collagen contraction inhibitor of this invention is advantageous for use in the treatment of keloid scars and wounds.

DETAILED DESCRIPTION OF THE INVENTION

Figure 1:
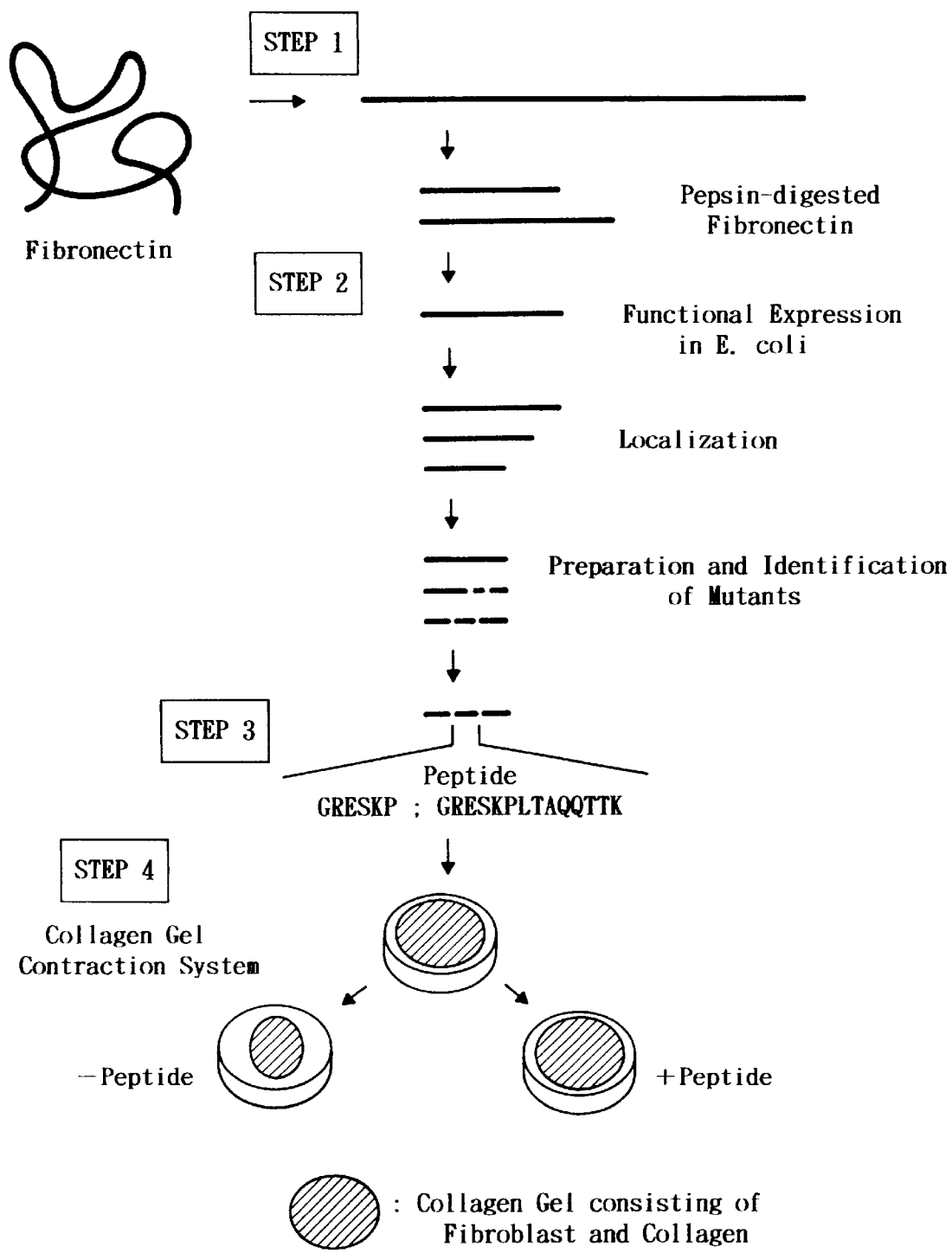
FIG. 1 is a block diagram illustrating the procedure for experimental studies conducted to identify the peptide of this invention (SEQ ID NOS. 1 and 2).

Peptides of this invention are based on a specific amino-acid sequence encoding fibronectin which was identified by the inventors in accordance with the following experimental study (refer to FIG. 1).

(1) Biochemical Analysis of Proteins (Step 1)

With an antibody scanning method based on a combined use of a plurality of known fibronectin antibodies and peptide maps with various proteases, the epitope of fibronectin recognized by the monoclonal antibody (A3A5) was localized. Using the information obtained, it was confirmed that the site of the fibronectin recognized by the A3A5 antibody is located between the gelatin-connecting domain and RGD sequence thereof. The inventors identified some of the A3A5 antibody reactive fragments from the pepsin-digested fibronectin, and determined the amino-acid sequence at the amino end of the fibronectin using a gas-phase peptide sequencer. Of these, two fragments were found to share the fourth ($III_4$) to sixth ($III_6$) regions of the III type repeats. This confirmed that the A3A5 antibody recognizes this approximately 30 kDa site.

The procedures as described above can be summarized as follows:

a) definitive degradation of purified plasma type fibronectin with a protease, pepsin;

b) detection of the fibronectin fragments recognized by the A3A5 antibody by the Western immunoblotting technique; and c) sequencing of the amino end region of the pepsin fragments by a gas-phase peptide sequencer.

(2) Molecular Biological Analysis (Step 2)

The inventors also established that the A3A5 antibody show a strong reactivity to the expression products from *E. coli* transformant containing the fibronectin fragment identified in Step 1. Based on this finding, it was proven that the A3A5 antibody recognizes the peptide in the $III_4$ to $III_6$ regions of fibronectin. Simultaneously, it was shown that the region of carbohydrates within fibronectin is not involved in the specific antibody recognition.

The $III_4$ to $III_6$ regions of fibronectin (approximately 270 amino acid residues: Sequence ID No. 3) was functionally expressed in *E. coli*, and by applying the site-directed mutagenesis (Nucleic Acids Research, 17, 6545, 1989), the localized pepsin fragments to be recognized by the A3A5 antibody were identified with various antibody-recognized mutants as an indicator.

The Specific procedures adopted will be shown below:

d) production of pepsin fragments in *E. coli* transformed with the fibronectin coding genes;

e) confirmation of the A3A5 antibody recognition to the fragments by using the Western immunoblotting technique;

f) localization of pepsin fragments using the functional expression;

g) preparation of the mutants of the localized pepsin fragments by the site-directed mutagenesis;

h) confirmation of the A3A5 antibody recognition to the fragments by using the Western immunoblotting technique; and i) identification of the mutants which have lost antibody recognition.

(3) Biochemical Analysis of Peptides (Step 3)

By referring to the known structural analysis data (the three-dimensional structure of the tenth type III module of fibronectin: an insight into RGD-mediated interaction, 71, 671–678, 1992), the looped structure of the pepsin fragments identified in Step 2 was deduced, so that the peptide portion constructing this deduced looped structure was identified in the pepsin fragment The inventors established that the peptide site recognized by the A3A5 antibody is the portion of the amino acid sequence from the 80th to the 85th in Sequence ID No. 3. Thereafter, the peptide consisting of these 6 amino acid residues (Sequence ID No. 1) was chemically synthesized by the known method. In addition, the peptide consisting of the amino acid sequence of Sequence ID No. 2 was similarly synthesized, which has an additional 8 amino acid residues with the Sequence ID No. 1.

The specific procedures adopted will be given below:

j) deduction of the looped structure in the localized pepsin fragment by checking it with the known structural analysis data; and k) chemical synthesis or the peptide which comprises the deduced looped structure.

(4) Cellular Biological Analysis (Step 4)

Studies were made as to the effectiveness of the synthesized peptides of Sequence ID Nos. 1 and 2 using a collagen gel contraction system (Experimental Cell Research, 193, 167–174, 1991). It was confirmed that the synthesized peptides have the effect of inhibiting the contraction of collagen gel. The analytical processes involved will be shown below:

l) studies on the effect of synthesized peptide upon collagen gel contraction system of fibroblast; and m) confirmation of the inhibition of collagen gel contraction by the synthesized peptide.

As noted above, the peptide of this invention is a novel active peptide, with their amino-acid sequence having been determined and their specific effects confirmed as a result of the experiments by the inventors.

The peptide of this invention is that comprising the amino acid sequence as shown in Sequence ID No. 1, and can be chemically synthesized by, for example, known the solid-phase peptide synthesis method (Journal of Chemical Society Perkin I, 538, 1981). More specifically, amino acid anhydrides of which amine functional groups are protected with Fmoc groups are prepared, and then the Fmoc-proline anhydride cooresponding to the C-terminal amino-acid residue is fixed to a resin. The resin is washed to remove the protecting group of the amine functional group of the C-terminal amino acid. Thereafter, the Fmoc-lysine anhydride, which is corresponding to the second amino-acid residue in the C-terminal of the amino-acid sequence of the peptide, is coupled to the unprotected amine functional group of the first amino acid already fixed. Similarly, successive amino acids, up to the sixth, are fixed. After coupling of all the amino acids is completed and the peptide chain having the target amino-acid sequence is formed, the protective groups other than acetoamidomethyl are removed and the peptide is released with a solvent. Finally, the peptide is purified by high performance liquid chromatography, for example.

Alternatively, the peptide of this invention can be obtained by hydrolyzing fibronectin with enzyme and separating and purifying the resulting active fractionations with chromatography. The peptide produced by either method do not have any risk to animals and human, since the amino acid sequence thereof is identified in fibronectin, one of the proteins constructing organisms, as described above.

Then, a collagen contraction inhibitor of this invention can be produced using the above described peptide, its pharmacologically acceptable derivatives, its pharmacologically acceptable salts, or a mixture thereof as its effective constituents. Of these, the peptide derivatives include those with amide at the N-terminal of the peptide and those with ester at the OH-terminal, and can be prepared by known methods. The pharmacologically acceptable salts can be prepared by inorganic acids, including hydrochloric acid, hydrobromic acid, sulfuric acid, nitric acid, phosphoric acid, and boric acid, as well as organic acids, including formic acid, acetic acid, propionic acid, trifluoroacetic acid, oxalic acid, succinic acid, maleic acid, fumaric acid, lactic acid, maleic acid, citric acid, and salcylate.

The collagen contraction inhibitor of this invention can be made into medicine by mixing the effective ingredient as described above and, for instance, pharmacologically acceptable excipients and solvents. When such medicine is to be employed for treatment of keloid scars and wounds, it can be directly applied or sprayed to the skin. It can be appreciated that this collagen contraction inhibitor is composed substantially solely of peptides, and can be applied as research reagent for the molecular biological, and cellular biological elucidation of the functions of collagen and fibronectin in the construction of cells.

What is claimed is:

1. A peptide having an ability to inhibit contraction of a collagen gel consisting at least of fibroblast and collagen, which peptide consists of the amino acid sequence of SEQ ID No. 1, or a pharmacologically acceptable salt thereof.

2. A peptide having an ability to inhibit contraction of a collagen gel consisting at least of fibroblast and collagen, which peptide consists of the amino acid sequence of SEQ ID No. 2, or a pharmacologically acceptable salt thereof.

3. A composition comprising the peptide or its pharmacologically acceptable salt according to claim 1 together with a pharmaceutically acceptable excipient or solvent.

4. A composition comprising the peptide or its pharmacologically acceptable salt according to claim 2 together with a pharmaceutically acceptable excipient or solvent.

5. A method for inhibiting contraction of a collagen gel consisting at least of fibroblast and collagen, which comprises adding an effective amount of a peptide consisting of the amino acid sequence of SEQ ID No. 1 to the collagen gel.

6. A method for inhibiting contraction of a collagen gel consisting at least of fibroblast and collagen, which comprises adding an effective amount of a peptide consisting of the amino acid sequence of SEQ ID No. 2 to the collagen gel.

* * * * *